United States Patent [19]

MacArthur

[11] Patent Number: 5,127,920
[45] Date of Patent: Jul. 7, 1992

[54] PROSTHESIS AND METHODS FOR SUBTOTAL DOME ARTHROPLASTY OF THE HIP JOINT

[76] Inventor: A. Creig MacArthur, 1405 Oakcrest La., Provo, Utah 84604

[21] Appl. No.: 413,550

[22] Filed: Sep. 27, 1989

Related U.S. Application Data

[63] Continuation of Ser. No. 290,855, Dec. 28, 1988, abandoned, which is a continuation of Ser. No. 31,985, Mar. 27, 1987, abandoned.

[51] Int. Cl.⁵ .......................... A61F 2/34; A61F 2/32
[52] U.S. Cl. ........................................ 623/22; 623/18
[58] Field of Search ...................... 623/16, 18, 19, 20, 623/21, 22, 23, 66, 901

[56] References Cited

U.S. PATENT DOCUMENTS

| | | | |
|---|---|---|---|
| 3,889,299 | 6/1975 | Osborne | 3/1 |
| 3,889,300 | 6/1975 | Smith | 623/21 |
| 3,974,527 | 8/1976 | Shersher | 3/1.912 |
| 4,123,806 | 11/1978 | Amstutz et al. | 3/1.912 |
| 4,151,615 | 5/1979 | Hall | 623/20 |
| 4,224,698 | 9/1980 | Hopson | 3/1.912 |
| 4,310,931 | 1/1982 | Müller | 3/1.912 |
| 4,404,692 | 9/1983 | Eftekhar | 3/1.912 |
| 4,532,661 | 8/1985 | Halpern | 623/23 |
| 4,536,894 | 8/1985 | Galante et al. | 623/22 |
| 4,662,888 | 5/1987 | Field | 623/20 |

FOREIGN PATENT DOCUMENTS

| | | | |
|---|---|---|---|
| 0201651 | 11/1986 | European Pat. Off. | 623/21 |
| 2845231 | 5/1979 | Fed. Rep. of Germany | 623/22 |
| 2933141 | 4/1980 | Fed. Rep. of Germany | 623/18 |
| 3332354 | 3/1985 | Fed. Rep. of Germany | 623/20 |
| 3516743 | 11/1986 | Fed. Rep. of Germany | 623/23 |
| 1287526 | 2/1962 | France | 623/22 |
| 2445136 | 8/1980 | France | 623/18 |
| 1526941 | 10/1978 | United Kingdom | 623/20 |

OTHER PUBLICATIONS

Brown et al., "A Contact-Coupled Finite Element Analysis of the Natural Adult Hip," 17 J. Biomechanics, 437-448 (1984).
Poss, M. D., "Current Concepts Review, The Role of Osteotomy in the Treatment of Osteoarthritis of the Hip," 66-A The Journal of bone and Joint Surgery, 144-151 (1984).
Oonishi et al., "Mechanical Analysis of the Human Pelvis and Its Application to the Artificial Hip Joint—By Means of the Three Dimensional Finite Element Method," 16 J. Biomechanics, 427-444 (1983).
Brown et al., "In Vitro Contact Stress Distribution in the Natural Human Hip," 16 J. Biomechanics, 373-384 (1982).
Pedersen, et al., "An Axisymmetric Model of Acetabular Components in Total Hip Arthroplasty," 15 J. Biomechanics, 305-315 (1982).
Jorring, "Osteoarthritis of the Hip," 51 Aeta Orthop. Scand., 523-530 (1980).
Radin, M. D., "Biomechanics of the Human Hip," 152 Clinical Orthopaedics and Related Research, 28-34 (1980).

(List continued on next page.)

Primary Examiner—David J. Isabella
Attorney, Agent, or Firm—Workman, Nydegger & Jensen

[57] ABSTRACT

Prostheses and methods are described for replacement of the dome areas of the hip joint. A femoral component is provided with a superior articular surface which is curved so as to simulate the shape of the dome area of the patient's femoral head. The damaged or diseased portion of the weight bearing dome area of the femoral head is removed and the femoral component is implanted. An acetabular component is also provided with an inferior curved articular surface which is generally congruent with the superior articular surface. The acetabular component is implanted in a recess formed in the patient's acetabulum. The position of the acetabular component is chosen to correspond to the location of the implanted femoral component when the joint is in a weight bearing posture. By use of the components, and the accompanying method, a subtotal hip dome arthroplasty may be effected.

28 Claims, 5 Drawing Sheets

OTHER PUBLICATIONS

Armstrong, et al., "In Vitro Measurement of Articular Cartilage Deformations in the Intact Human Hip Joint Under Load," 61-A *The Journal of Bone and Joint Surgery*, 744-755 (1979).

Carlsson, J. et al., "Bone Mass in Primary Coxarthrosis," 50 *Acta. Orthop. Scand.*, 187-189 (1979).

Arnoldi, et al., "The Pathomechanism of Human Coxarthrosis," Supplementum No. 181 *Acta Orthopaedica Scandinavaci*, 5-46.

Cameron, et al., "Observations on Osteoarthritis of the Hip Joint," *Clinical Orthopaedics and Related Research*, 31-40 (1975).

Jeffery, et al., "Osteophytes and the Osteoarthritic Femoral Head," 57-B *The Journal of Bone and Joint Surgery* 314-324 (1975).

Day, et al, "Contact Pressures in the Loaded Human Cadaver Hip," 57-B *Journal of Bone and Joint Surgery*, 302-313 (1975).

Byers, "The Effect of High Femoral Osteotomy on Osteoarthritis," 56-B *The Journal of Bone and Joint Surgery*, 279-290.

Morscher, "Intertrochanteric Osteotomy in Osteoarthritis of the Hip," *Surgical Treatment of Degenerative Arthritis of the Hip*, 24-46 (date unknown).

Sokoloff, Leon, "The General Pathology of Osteoarthritis," from Institute of Orthopaedics publication (London 1974).

Bullough, et al., "The Relationship Between Degenerative Changes and Load-Bearing in the Human Hip," 55-B *The Journal of Bone and Joint Surgery*, 746-758 (1973).

Meachim, "Articular Cartilage Lesions in Osteo-Arthritis of the Femoral Head," 107 *J. Path.*, 199-210 (1972).

A. S. Greenwald et al., "Weight-Bearing Areas in the Human Hip Joint," vol. 54B, No. 1, *The Journal of Bone and Joint Surgery*, 157-163 (Feb. 1972).

Carl C. Arnoldi et al., "Venous Engorgement and Intraosseous Hypertension in Osteoarthritis of the Hip," vol. 54B, No. 3, *The Journal of Bone and Joint Surgery*, 409-421 (Aug. 1972).

Albert B. Furguson, Jr., M.D., "The Pathology of Degenerative Arthritis of the Hip and the Use of Osteotomy in its Treatment," No. 77, *Degenerative Arthritis of the Hip*, 84-97 (Jun. 1971).

A. S. Greenwald et al., "The Transmission of Load Through the Human Hip Joint," vol. 4, *J. Biomechanics*, 507-528 (1971).

Henry J. Mankin, M.D. et al., "Biochemical and Metabolic Abnormalities in Articular Cartilage from Osteo-Arthritic Human Hips," vol. 53-A, No. 3, *The Journal of Bone and Joint Surgery*, 523-537 (Apr. 1971).

J. P. Gofton, M.D., F.R.C.P.[C], F.A.C.P., "Studies in Osteoarthritis of the Hip," vol. 104, No. 8, *C.M.A. Journal*, 679-1011 (Apr. 17, 1971).

P. D. Byers, et al., "A post mortem Study of the Hip Joint Including the Prevalence of the Features of the Right Side," vol. 29, *Annals of the Rheumatic Diseases*, 15-31 (1970).

M. H. M. Harrison et al., "Osteoarthritis of the Hip: A Study of the Nature and Evolution of the Disease," vol. 35B, No. 4, *The Journal of Bone and Joint Surgery*, 598-626 (Nov. 1953).

Radin, E. L. et al., "The Mechanics of Joints as it Relates to Their Degeneration," Symposium on Osteoarthritis 34-43 (date unknown).

Houglund, F. T., "Osteoarthritis of the Hip: Etiologic Factors and Preventative measures," Symposium Osteoarthritis 66-79 (date unknown).

Rydell, N., "Intravital Measurements of Forces Acting on the Hip Joint," (source and date unknown).

S. A. V. Swanson, et al., "Laborator Tests on Total Joint Replacement Prostheses," 55-B *The Journal of Bone and Joint Surgery*, 759-773 (1973).

PROSTHESIS AND METHODS FOR SUBTOTAL DOME ARTHROPLASTY OF THE HIP JOINT

This application is a continuation of U.S. Pat. application Ser. No. 07/290,885, filed Dec. 28, 1988, which is a continuation of U.S. Pat. application Ser. No. 07/031,985, filed Mar. 27, 1987, now abandoned, for PROSTHESES AND METHODS FOR SUBTOTAL DOME ARTHROPLASTY OF THE HIP JOINT.

I. BACKGROUND

A. The Field of the Invention

This invention relates to prosthetic structures and corresponding surgical methods used to relieve pain caused by disorders of the hip joint. More particularly, the invention relates to prostheses and methods for the subtotal dome arthroplasty of the hip joint.

B. Background Discussion

The hip is one of the most versatile joints of the human body and serves an essential function in allowing an individual to lead a normal life. The human hip joint performs its function much better than any device heretofore designed by human engineers. The hip joint withstands forces which are not readily apparent to those unfamiliar with orthopedics. For example, during ordinary walking, the hip joint is routinely subjected to dynamic forces nearly four times greater than body weight. The dynamic forces on the hip joint may be as great as ten times body weight during activities such as running or jumping.

The bones of the hip joint, when functioning properly, move together with very little friction. To function properly, a healthy hip joint requires an intact layer of hyaline cartilage, the material which makes up the articular cartilage on the opposing surfaces of the joint. Also, the bones of the joint must be in proper alignment and the synovial membranes must produce suitable amounts of lubricating (synovial) fluid. Furthermore, the joint structures must prevent the bones from being placed in an abnormal position.

FIG. 1 is an anterior (that is, taken from the front of the body) cross-sectional view of the human hip. In FIG. 1, the semicircular shape of actabulum 11 can be seen. The upper leg bone, or femur 16, which can be seen just below illium 10, is the longest and strongest bone in the body. The upper end of the femur is provided with a head 14, a neck 18, a greater trochanter 17, and a laser trochanter 15. The speroidally-shaped femoral head is shown in FIG. 1 in a "normal" relationship with the acetabulum. It should be appreciated that FIG. 1 is not intended to show the exact structures of the hip joint, since this structure varies somewhat from individual to individual, but to show the relationship of the major components which make up the hip.

FIG. 1 also illustrates the acetabulum articular cartilage 12 and femoral head articular cartilage 19. A space is shown extending between the entirety of the two articular surfaces. This "joint space" may or may not be present in a particular hip depending upon the condition of the hip. Normally, the articular cartilage is smooth and intact. When the articular cartilage is damaged, pain and an accompanying restriction of motion will usually result.

The femur is provided with a femoral neck which may be up to five centimeters long. The femoral neck separates the shaft of the femur from the femoral head. This arrangement allows the femur a substantial degree of movement without interference from the bones making up the pelvis.

The greater trochanter serves as an attachment point for various muscles and ligaments. The lesser trochanter serves a similar purpose. Round ligament 13 is thought to provide a passage for the blood vessels to the femoral head and also assist with spreading of synovial fluid over the joint surfaces to lubricate and nourish the cartilage. The versatility of the hip joint can be appreciated by realizing that the normal motion of the hip joint includes flexion and extension (rotation in forward and rearward directions, respectively) and adduction and abduction (motion towards the median (center) line of the body and away from the center line of the body, respectively).

While the hip joint generally serves its purpose very well, various disorders of the hip cause a great deal of pain and loss of mobility and function to those who are afflicted with such disorders. Some hip disorders are congenital; that is, they are present at birth. Other disorders of the hip are brought on by bacterial infections which may occur at any age. Perhaps the most widespread disorder of the hip is arthritis. The term "arthritis" is generally used as a common name for the effects of several degenerative hip disorders.

Of the various types of arthritis, osteoarthritis is perhaps the most common. Osteoarthritis is a degenerative "wear and tear" process that affects substantial numbers of people. The final result of unchecked osteoarthritis is damaged articular cartilage which in many cases causes extreme pain as the damaged cartilage surfaces are rubbed together during joint movement. It has been estimated that between 8% and 15% of the populations in developed countries, with higher percentages prevalent in older populations, suffer from some degree of osteoarthritis.

One disorder of the hip which appears to lead to osteoarthritis is known as "congruence". Congruence is a term used to describe a condition in which the shape of the femoral head and the shape of the acetabular socket become matched so that dome area of the acetabulum and the femoral head are nearly always in contact. Congruence of the hip can cause increased wear on the joint surfaces. Several of these disorders and other conditions are explained in more detail hereinbelow.

Osteoarthritis may also involve the development of abnormal bony outgrowths on the joint surfaces known as osteophytes. An osteophyte consists of a lump of "cancellous" tissue (tissue having a lattice structure similar to the spongy tissue of the bone) which is capped by a sheet of soft tissue. Commonly, cysts also form on the femoral head and in the acetabulum of the hip joint. These cysts often form just under the articular cartilage and result in a great deal of pain.

Generally, osteoarthritis affects people past the age of 60 years without providing an easily recognizable single cause. However, osteoarthritis may develop in younger people due to a congenital condition or disease. Furthermore, traumatic injury may cause the development of an osteoarthritic condition.

Another hip disorder is osteonecrosis, or death of a portion of a bone, which is due to an insufficient blood supply to part of, or the whole of, a bone. Osteonecrosis may be brought on by excessive alcohol consumption, administration of particular drugs, old age, or as a result of osteoarthritis.

In the prior art, several methods have been used for alleviating the pain and improving the function of a hip joint afflicted with a degenerative disorder such as osteoarthritis.

Perhaps the earliest surgical procedure used to reduce pain due to a disorder of the hip joint was "ankylosing," or fusing, the joint. This alternative, generally called arthrodesis, alleviates pain in a diseased hip joint but also prohibits any proper functioning of the joint. Thus, arthrodesis is generally not an acceptable procedure of relieving hip pain to most patients. In fact, hip surgery is quite often carried out in order to remedy a hip which has become ankylosed, stiff, or immovable.

In some other cases, "debridement" of a hip joint may be helpful. Debridement of the joint usually consists of removing unwanted bony spurs and loose pieces of bone and cartilage within the joint cavity. While this procedure is helpful in some cases, the most common cause of pain and loss of function is due to degeneration of the hip joint rather than abnormal growths or debris in the joint.

Osteotomy, which generally refers to the cutting and resetting of a bone, has also been used in an attempt to alleviate pain and restore function of the hip joint. By cutting and resetting the femur, for example, it may be possible to reorient the head of the femur within the acetabulum such that portions of the femur head not affected by the degenerative disorder are used as weight-bearing surfaces. However, in the case of osteoarthritis, the surfaces of both the acetabulum and the head of the femur are generally involved in the degenerative condition. If the surface of the acetabulum has been damaged, repositioning of the femoral head will probably not provide relief.

Because of limitations of the foregoing procedures, one of the most common procedures used in treatment of hip disorders is the implantation of an artificial joint component. This procedure is known as "arthroplasty." Arthroplasty has been one of the major areas of advancement in hip surgery during the past quarter century. Hip arthroplasty has included techniques known as interpositional arthroplasty, partial arthroplasty, and total arthroplasty.

Interpositional arthroplasty of the hip joint generally involves interposing a layer of material between the two opposing articular surfaces of the joint. For example, materials such as muscle, fibrous tissue, celluloid, silver plates, rubber sheets, magnesium, zinc, decalcified bones, and pig's bladder have all been used in interpositional arthroplasty of various joints. Cup-shaped structures made from gold foil, glass, or VITALLIUM ® (a cobalt-chromium alloy) have also been interposed between the head of the femur and the acetabulum. Even further attempts have been made to encase the femoral head within a metallic shell and also line the acetabulum with a cup comprised of a plastic-like material.

Partial arthroplasty involves the replacement of one of the two opposing articular joint surfaces. For example, this procedure is used where the femoral head has been damaged but yet the acetabulum is otherwise normal. In such a case, it may be beneficial to replace the femoral head with an artificial prosthesis which will work in conjunction with the natural acetabulum. Partial arthroplasty has met with only limited success.

The most common arthroplasty procedure used to alleviate pain and restore hip function is total arthroplasty, also called a total hip replacement. While many different styles of hip replacement prosthesis have been implanted in patients, they generally resemble the prosthesis illustrated in FIG. 2. FIG. 2 also illustrates the femur and a portion of the pelvis in cross section in order to best show how the components of a total hip replacement are implanted in the body.

Conventional total hip replacement involves a complete internal amputation of the hip joint as suggested in FIG. 2. The conventional surgical procedure used during total hip replacement involves making a surgical incision to provide an approach to the hip. Once the hip is exposed, the joint is dislocated so that the femoral head and acetabular socket can be accessed. The femoral head and neck are then amputated. Often, the greater trochanter 32 is removed and reattached at a lower point by the use of wires 34. Once the femoral head and neck have been removed, the femoral canal (the central core of the bone, generally indicated at 26) is reamed so as to provide a cavity into which stem 36 of femoral component 20 may be inserted. The femoral canal is reamed so that its diameter is significantly larger than the diameter of femoral component stem 36.

The most commonly accepted method of fixing the femoral component to the femur is by polymethyl methacrylate (PMMA). PMMA is a two-component acrylic cement which has the advantage of exhibiting a rapid setting time. After mixing the two components, the femoral canal is "packed" with unset PMMA. The stem 36 of femoral component 20 is then inserted into the femoral cavity and the femoral component 20 is held in the proper position until the PMMA has set. Since the femoral canal has been reamed out to a larger diameter than the shaft of the femoral component, the PMMA cement serves as a "grout" 36, interfacing between the shaft and the remaining bone.

The femoral components are available in a variety of sizes and styles, but nearly all those used presently include stem 22, neck 28, and ball-shaped head 30 portions similar to those pictured in FIG. 2. Most of the prosthetic femoral components used presently are fabricated from a cobalt-chromium steel alloy or a titanium alloy.

Ideally, a prosthetic femoral component should exhibit characteristics identical to that of living bone, although conventional prostheses have not equalled normal bone tissue. Problems of fatigue, breakage, and loss of fixation of the femoral component are common following total hip replacement.

Implantation of the acetabular component also requires significant alteration of the bone structure. The acetabulum is first reamed out to provide a cup-shaped cavity into which the acetabular component, generally indicated at 22 in FIG. 2, will be fixed. Conventional acetabular components 22 used in total hip replacements are relatively large. Presently, most acetabular cups are fabricated of ultra-high molecular weight polyethylene (UHMWP). The acetabular component 22 is fixed within the reamed out cavity by PMMA adhesive once again acting as a grout.

After femoral component 20 and acetabular cup 22 have been implanted, the greater trochanter 32, if previously removed, is reattached using wires 34 at a point lower on the femur so as to provide a mechanical advantage more favorable to the total hip prosthesis. The joint is then reduced and the surgical incision closed.

While the conventional total hip prosthesis procedure has been popularly accepted, there still exist major risks and drawbacks that accompany its use. First, the total hip replacement procedure can be characterized as an internal amputation of the femoral neck, head, and acetabulum. A great deal of bone, which in many cases is healthy and potentially usable, is removed and lost.

Furthermore, to insert the femoral component, the femoral canal must be severely invaded. The femoral canal is a region with substantial blood flow and numerous blood vessels; invading this area causes a great deal of blood loss. It is not uncommon for a patient to require four to eight units of blood during the procedure. A total hip replacement, even when efficiently carried out, is a complicated procedure often requiring the patient to remain in surgery for a prolonged period of time.

As mentioned earlier, the most common method of fixing the components of a total hip prostheses in place is by the use of polymethyl methacrylate (PMMA). PMMA cement is prepared by mixing two components together which harden into a solid mass by way of a chemical process. One of the two components is a fine granular powder of prepolymerized polymethyl methacrylate and the other component is a liquid monomer.

One of the constituents of the liquid monomer is N,N-Dimethyl-Para-Toluidine (DMPT), a toxic material. Other monomer ingredients also exhibit adverse effects on humans. Thus, the introduction of the mixed, but as yet unset, PMMA cement mixture into the femoral canal, an area rich in blood vessels, presents the potential of introducing a significant amount of toxic materials into the blood stream Known reactions to PMMA cement include hypotension and even circulatory system collapse.

Aside from the immediate hazards that attend the use of PMMA cement, concern has also been expressed that there may be long term toxicity, hypersensitivity, and carcinogenicity resulting from the materials that make up the prior art total hip prosthesis, including cobalt, chrome, titanium, and polyethylene. In view of the uncertainty of the effects of long term use of these materials within the human body, it has been considered advisable to reduce the contact between these materials and the body as much as possible.

In any surgical procedure there is the potential that infection may occur due to entry of microorganisms into the surgical wound. Devastating infections are particularly difficult to prevent in total hip replacement procedures due to the extensive invasion of the body that is required. Special surgical techniques have been developed which reduce the risk of an infection to the patient. Unfortunately, these surgical techniques require far greater care than other types of surgical procedures, and in some cases are extremely cumbersome.

As mentioned previously, the stresses on the hip joint during ordinary activities are very high. During strenuous activities those stresses are increased several fold. These high stresses result in several mechanical difficulties in a patient fitted with a conventional total hip prosthesis. For example, it is not uncommon for the femoral component to become dislocated from the acetabular component. Alternatively, the components may fail, i.e., fracture or break, due to the stresses placed upon them. A common difficulty is loosening of the components from the surrounding bone. Generally, problems such as loosening or failure are particularly acute with the femoral component. Furthermore, not only does loosening or failure of the prosthesis present a danger to the patient, but due to the procedures performed on the surrounding bone, and the additional stress placed on the bone because of the use of the prosthesis, those bone structures supporting the prosthesis components may be subject to an increased chance of fracture and undue wear.

Because of these difficulties the maximum useful life of an implanted prosthesis is frequently less than 8 to 12 years. In individuals less than 40 years of age, the average useful life of a conventional prosthesis is often only about 4 to 6 years.

Once total hip replacement has occurred, revision of the procedure (revision being the term used to describe when the prosthesis is replaced), can be extremely difficult due to the amount of bone mass which was removed during the original procedure. Also, a revised total hip replacement has a much shorter useful life than the original replacement. Still further, the bone structure, as mentioned earlier, may become weakened due to the additional stresses placed upon them by the prosthesis and due to any effects which at the present time are unknown, such as delayed hypersensitivity to the materials used in the prosthesis Because of the relatively short expected life of a prosthesis multiple replacements would be necessary over the lifetime of a younger patient.

In view of the above difficulties inherent in the total hip replacement structures and procedures as carried out in the prior art, it would be a significant advance in the art to provide prosthetic structures and methods to reduce or eliminate pain inherent in an osteoarthritic hip joint, and to improve the function of such a hip joint, while avoiding the hazards and risks inherent in the presently used total hip replacement procedure.

It would be a further advancement in the art to provide prosthetic structures and a simplified surgical procedure which are as noninvasive as possible and minimize the removal of healthy bone mass. It would be particularly beneficial if blood loss during hip replacement could be substantially decreased.

Furthermore, it would be a significant benefit to provide hip prosthetic structures and accompanying procedures which minimize the amount of nonbiological material to be implanted in the body.

Still further, providing hip prosthetic structures and procedures which present a minimal risk of loosening or failing over a long period of time and subject to the problem of dislocation presently observed in the conventional prosthetic devices, would be a welcome advance in the art.

It would also be a significant advance in the art to provide hip prosthetic structures and procedures which would allow the choice of several alternatives if revision of the initial implant becomes necessary.

Furthermore, providing hip prosthetic structures which are simpler to manufacture and cost less than those prostheses available in the prior art, would be another advance in the art.

These and other benefits are obtained by the structures and methods for subtotal hip dome arthroplasty of the present invention.

II. BRIEF DESCRIPTION OF THE DRAWINGS

Figures 5A, 5B, 5C:
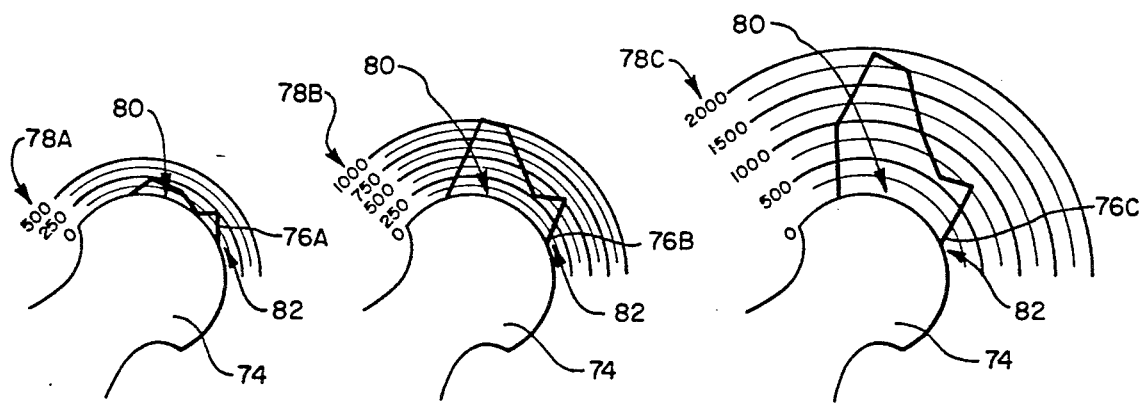

FIGS. 5A, 5B, and 5C are diagrams representing the calculated intraarticular contact stress for a normal human hip.

Figure 6:
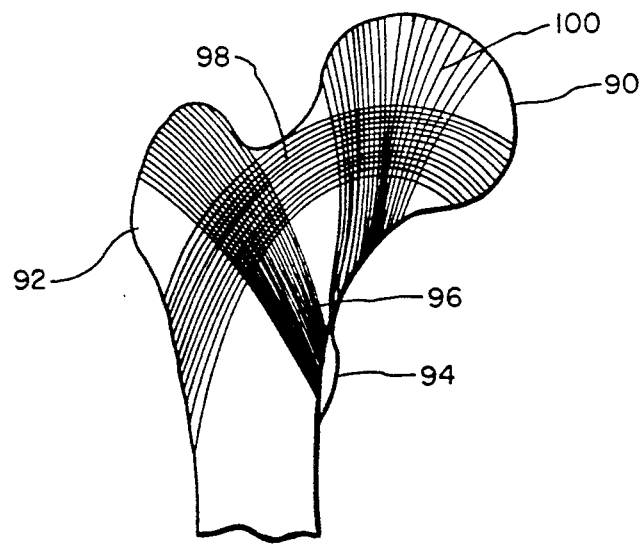

FIG. 6 is a cross-sectional representation of a normal human femoral head and neck showing the trabecular stress lines.

Figure 7:
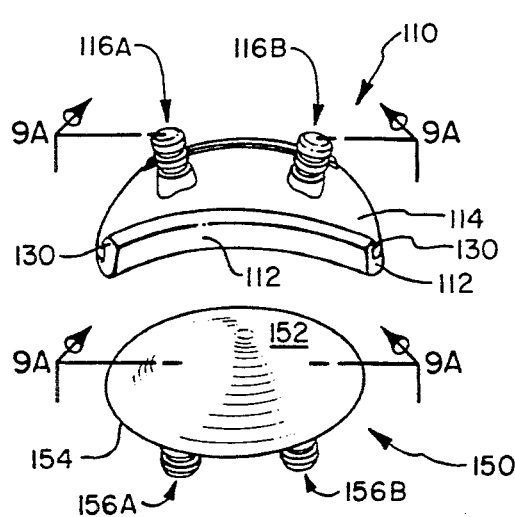

FIG. 7 is a superior (top) perspective view of the femoral and acetabular components of a presently preferred embodiment of the present invention.

Figure 8:
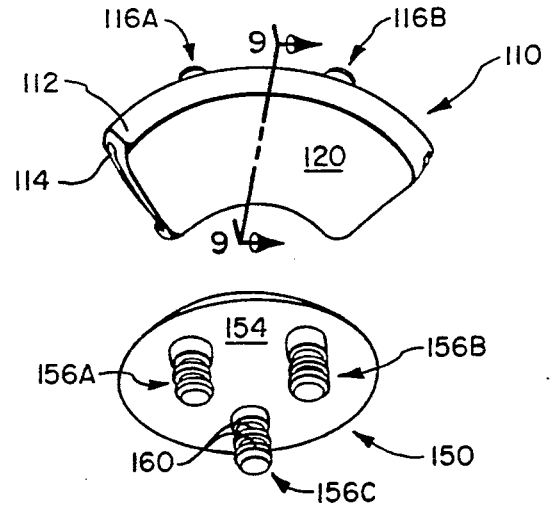

FIG. 8 is an inferior (bottom) perspective view of the femoral and acetabular components of the embodiment shown in FIG. 7.

Figure 9:
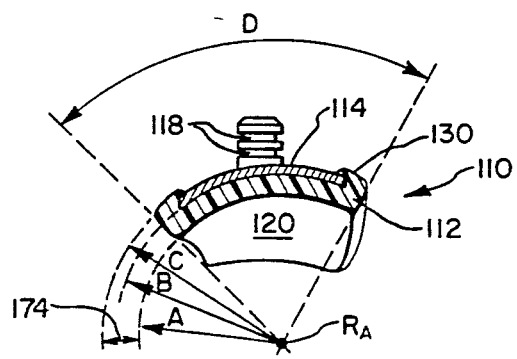

FIG. 9 is a cross-sectional view of the embodiment illustrated in FIGS. 7 and 8 taken along line 9—9 of FIG. 8.

Figure 9A:
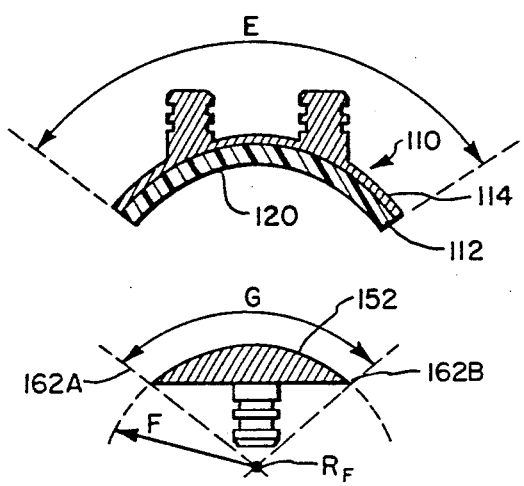

FIG. 9A is a cross-sectional view of the embodiment illustrated in FIGS. 7 and 8 taken along line 9A—9A of FIG. 7.

Figure 10:
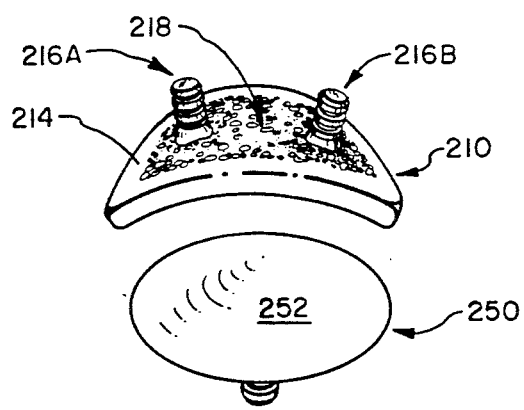

FIG. 10 is a superior perspective view of another presently preferred embodiment of the present invention.

Figure 11:
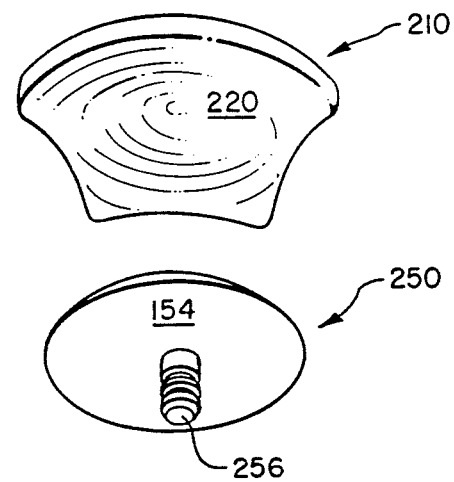

FIG. 11 is an inferior perspective view of the embodiment illustrated in FIG. 10.

Figure 12:
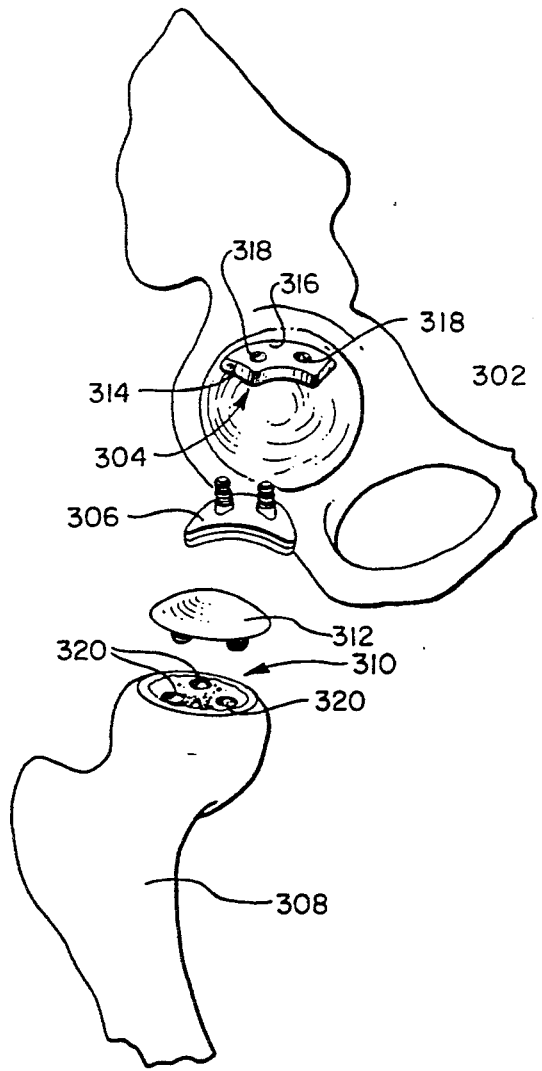

FIG. 12 is a perspective view of the femoral component ready to be fixed in place on the femoral head and the acetabulum ready to be implanted with the acetabular component.

Figure 13:
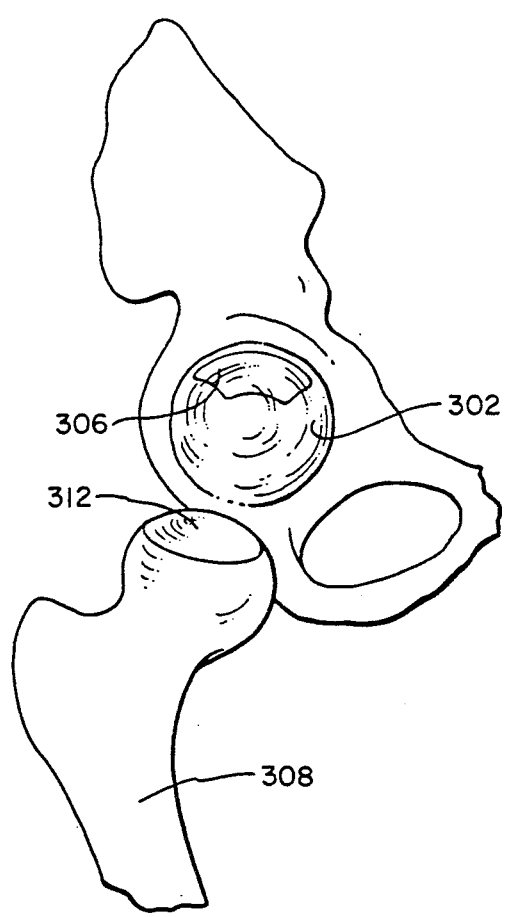

FIG. 13 is a perspective view of the femur and acetabulum repaired with the femoral and acetabular components, respectively, of the present invention.

Figure 14:
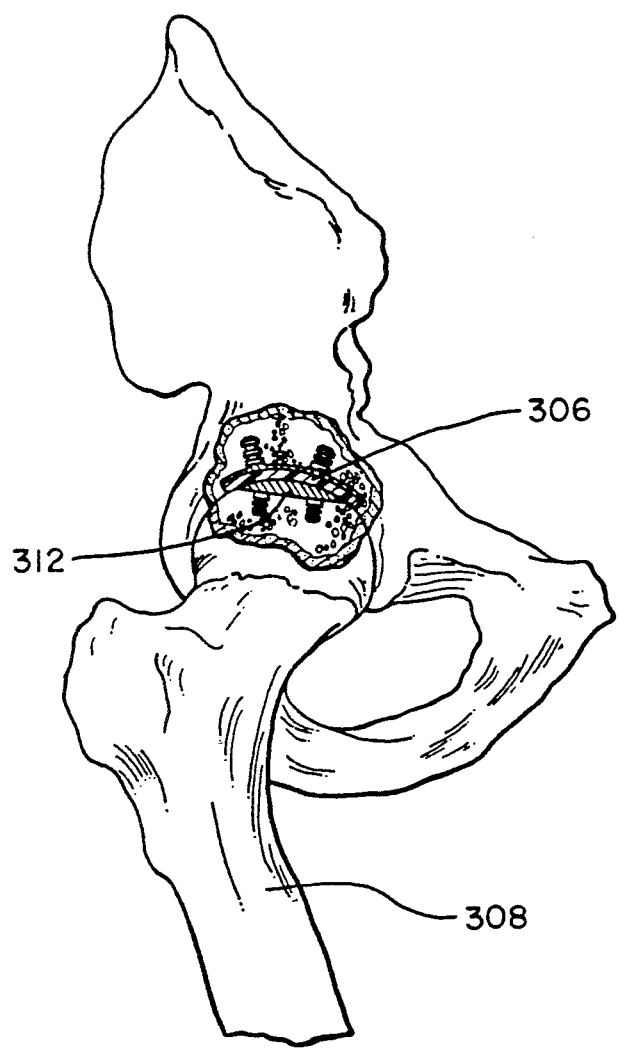

FIG. 14 is a partially cut-away perspective view of the hip joint with the prosthetic structures of the present invention implanted.

III. BRIEF SUMMARY AND OBJECTS OF THE INVENTION

The present invention encompasses structures and methods for subtotal arthroplasty of the hip joint. Various factors indicate that pain due to osteoarthritis and other degenerative hip disorders often stems from the involvement of the dome regions of both the acetabulum and the femoral head in the degenerative condition.

The present invention includes both a femoral component and an acetabular component. These components are intended to replace only the portions of the dome regions of the articular surfaces that are diseased, and to leave healthy tissues intact. The materials from which the components are fabricated are chosen with considerations in mind such as the biocompatibility of the materials, their structural strength, and the low friction characteristics of the material or materials, as well as other considerations.

In order to fix the femoral component in place, the dome area of the femoral head is removed. The articular surface of the femoral component, which is shaped to approximate the curvature of the dome area of the femoral head, is fixed on the femoral head so as to face slightly antero-superiorly. A portion of the dome region of the acetabulum is excised to a shape and depth which matches the shape and the thickness of the acetabular component of the present invention. The acetabular component is then implanted in an inlaid fashion in the area which was excised from the acetabulum.

By replacing the dome regions of both the femoral head and the acetabulum, the areas of the hip joint articular surfaces which experience the greatest stress during standing and walking are replaced. Thus, pain will be reduced and hip function increased after the structures have been implanted in the hip joint which was heretofore affected by a degenerative disorder.

In view of the foregoing, it is a primary object of the present invention to provide structures and methods for reducing pain due to degenerative disorders of the hip. In particular, it is a primary object of the present invention to provide structures and methods for replacing the dome areas of the femoral head and acetabulum, generally referred to herein as subtotal hip dome arthroplasty, in order to reduce or eliminate pain, increase hip motion, and enhance function of the joint.

It is also an object of the present invention to provide structures and methods for repairing a damaged or diseased hip joint which require that only a relatively small amount of bone mass be removed.

It is another object of the present invention to provide structures and methods for reducing pain and increasing function of a diseased hip joint in which a minimal amount of blood is lost during the surgical procedure.

It is still another object of the present invention to provide structures and methods for repairing a damaged or diseased hip joint which are significantly less invasive than methods of hip arthroplasty found in the prior art.

A still further object of the present invention is to provide structures and methods for reducing pain and increasing function of a diseased hip joint in which foreign material presented to the body tissues and fluids is reduced to a minimum.

Another object of the present invention is to provide structures and methods for reducing pain and increasing function of a damaged or diseased hip joint which are less prone to structural failure than those structures and methods available for hip arthroplasty in the prior art.

Yet another object of the present invention is to provide structures and methods for reducing pain and increasing function of a diseased hip joint which do not place abnormal stresses upon the remaining bone mass during normal patient activities.

Another object of the present invention is to provide structures and methods for reducing pain and increasing function of a diseased hip joint which may be relatively easily and simply revised if wear or failure of the structures requires their replacement.

A further object of the present invention is to provide methods for reducing pain and increasing function of a diseased hip joint which are highly effective surgical procedures as well as providing structures that are low in cost to fabricate.

These and other objects of the present invention will become apparent during the description of the preferred embodiments which follows.

IV. DETAILED DESCRIPTION OF THE PREFERRED EMBODIMENTS

A. Introduction

The present invention includes prosthetic components and methods for surgically implanting such components in the human hip to reduce pain, improve motion, and enhance function of a diseased hip joint.

Generally, a patient postpones obtaining medical treatment until the pain due to a hip disorder is severe. By this time, both the acetabulum and the femoral head are generally involved in causing the patient pain and a corresponding reduction of hip motion and function.

Accordingly, it is generally necessary to take corrective action by treating both the femoral head and the acetabulum. The present invention includes both femoral and acetabular prosthetic components adapted for replacement of damaged tissue and bone. Generally, both components will be used in cooperation with each other, although there may be rare occasions when use of a single component may produce the desired result.

The following description is divided into several parts in order to improve the clarity of the description and also to assist the reader in understanding the concepts involved. First some of the significant causes of pain in the hip are examined so that it will be clear how the present invention helps to reduce or eliminate such pain and thus improve hip motion and function. Upon this foundation, a detailed description of the presently preferred embodiments of the present invention is provided together with a brief explanation of the protocols and procedures of the invention.

B. Localization of Hip Pain

Investigations into the causes and localization of a painful hip joint indicate that hip pain is often caused by degeneration of the articular cartilage surfaces in the dome areas of the femoral head and acetabulum. As used herein, reference made to the acetabular dome, femoral head dome, or femoral dome, should be understood as making reference to the superior portion of the articular cartilage surface of the femoral head or the articular cartilage surface of the acetabulum which is disposed superiorly to the femoral head dome when the patient is standing.

It should be appreciated that the FIGS of the drawings are meant to diagramatically represent the structures of the hip. Thus, many of the FIGS are stylized representations of the hip. Further, since the formation of a hip may significantly vary from individual to individual, the hip joint illustrated herein should be considered to be representative, and is not intended to be an exact representation. Because of these variations from hip joint to hip joint, the term "dome" cannot refer to a location with fixed dimensions but refers to a general anatomical location. The full meaning of the term "dome" will be appreciated by those skilled in the orthopedic arts and will become clearer during the subsequent discussion.

One indication that the dome areas are particularly involved in the genesis of hip pain is the examination of what is termed the congruency of the hip joint. FIGS. 3A-3B and 4A-4B illustrate a cross section of a human hip joint taken along a frontal plane of the body (a plane which would divide the body into anterior (front) and posterior (back) portions). In FIGS. 3A-3B and 4A-4B the femur is indicated at 58, and the illium at 52. The femoral head is indicated at 50 with the greater trochanter indicated at 60. The articular surface of the acetabulum is indicated at 56 while the articular surface of the femoral head is indicated at 54.

Figure 3A:
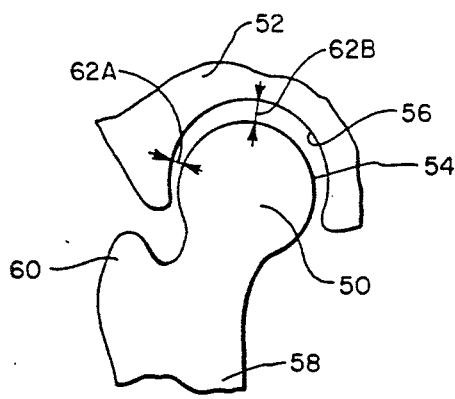
FIG. 3A is a diagrammatic representation of an incongruent human hip joint in an unloaded state.

FIG. 3A represents a normal hip joint in an unloaded (i.e., not weight bearing) state. As can be seen in FIG. 3A, the curvature of the articular surface of the acetabulum does not match the curvature of the articular surface of the femoral head. The mismatching or "incongruency" of the curvatures is demonstrated by the fact that the distance indicated by line 62A is less than the distance indicated by line 62B.

Figure 3B:
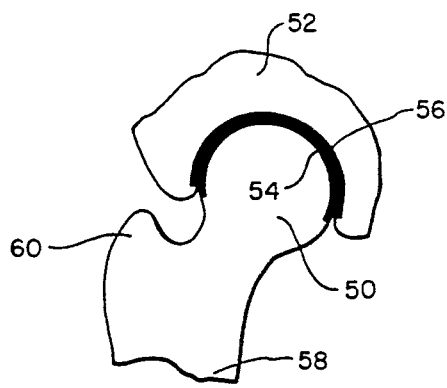
FIG. 3B is a diagrammatic representation of the human hip joint of FIG. 3A in a loaded state.

FIG. 3B is a view of the normal hip joint of FIG. 3A taken in a loaded (i.e., weight bearing) state. FIG. 3B might represent the hip joint when the individual is standing. As can be seen from FIG. 3B, the articular surface and the underlying bone of both the acetabulum and the femoral head deform under load to allow the curvature of the two articular surfaces to conform to one another. In this fashion, the load is distributed over a larger surface area, represented by the bold line, resulting in less stress per unit area on the articular surfaces of the joint. The condition represented in FIG. 3B, where substantially all of the articular surfaces are in contact, most likely occurs only intermittently such as during the push off and landing phases of a walk or run. During a stand, there is generally somewhat of a joint space still present in an incongruent hip. If no joint space is present during a stationary stand then the hip may be approaching a congruent condition.

FIGS. 3A and 3B indicate the condition generally found in a "normal" or "healthy" hip joint; the normal hip is incongruent in an unloaded state. Incongruency of a hip plays an important function in proper nourishment of the articular cartilage surfaces. Since the articular surfaces are incongruent, as the hip is moved, for example during walking, synovial fluid is swept over the articular surfaces by the action of the joint spaces which are created as the hip joint is moved and as it alternately is loaded and unloaded with body weight. Thus, incongruency of the human hip is an important feature of a normal hip required to keep the articular surfaces healthy and normal. Hip incongruency is believed to play other important roles in maintaining the articular cartilage.

Figure 4A:
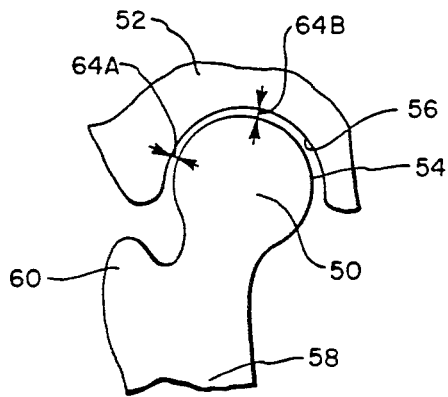
FIG. 4A is a diagrammatic representation of a congruent human hip joint in the unloaded state.

FIG. 4A is a schematic representation of a hip joint which, due to some disorder, has become congruent so that the articular surfaces of the acetabulum and femoral head are in contact in the unloaded state. The congruent condition is demonstrated by the distances indicated by lines 64A and 64B being the same, in contrast to the difference in the distances as seen by 62A and 62B in FIG. 3A.

Figure 4B:
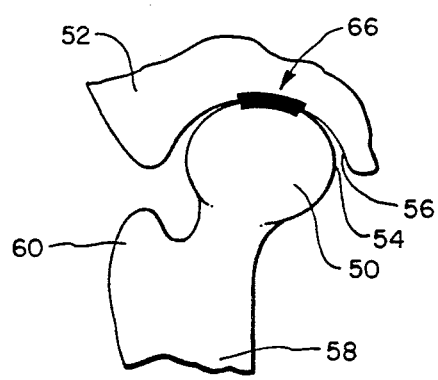
FIG. 4B is a diagrammatic representation of the congruent human hip joint of FIG. 4A in a loaded state.

FIG. 4B schematically represents the hip joint illustrated in FIG. 4A in a loaded condition. The contact area between the articular surfaces shown in FIG. 4B by the dark line indicated at arrow 66 represents the dome areas of the femoral head and acetabulum as discussed previously. Where the articular surfaces are congruent in an unloaded condition, the application of a load causes the acetabulum articular surface to deform in a manner similar to that shown in FIG. 3B. This deformation of the articular surfaces in a congruent hip causes the load to be distributed over a very small surface area of the articular surfaces, indicated at arrow 66, rather than over a large surface area is the case in an incongruent joint.

After hip congruency occurs, such a small portion of the articular surfaces bear such a large load that it is generally not long before wear occurs to the dome areas of the articular surfaces resulting in osteoarthritis and its accompanying pain. This problem is aggravated because without the joint spaces which are present in a healthy incongruent hip joint proper distribution of synovial fluids across the articular cartilage cannot be accomplished. Degeneration of the articular surfaces in the dome area 66 generally follows shortly after congruency of a hip has occurred.

Biomechanical studies are useful in identifying the locations of the articular surfaces of the hip joint subject to the greatest stress, and thus those areas at greatest risk. FIGS. 5A, 5B, and 5C are diagrammatic representations of the stresses placed upon the articular surfaces of a normal hip under conditions of standing, walking, and running, respectively. The femoral head is represented by the outline marked 74. This outline represents a cross-sectional view of the femoral head taken along a sagittal plane of the body (the plane taken from the front to the rear of the body). The information displayed in FIGS. 5A–5C indicates the calculated value of contact stress between the articular surface of the acetabulum and the articular surface of the femoral head in a normal hip joint in pounds per square inch. For a discussion of the procedure used to obtain the values indicated and additional information see T. D. Brown and A. M. DiGioia III, *A Contact-Coupled Finite Element Analysis of the Natural Adult Hip*, 17 J. Biomechanics 427–448 (1984), incorporated herein by reference.

The contour stress lines, marked 76A, 76B, and 76C, respectively, indicate the pressure (force divided by area) applied to a finite region of the surfaces under three different conditions. The pressure is indicated in pounds per square inch (psi) by scale markings generally indicated at 78A, 78B, and 78C, respectively.

FIG. 5A illustrates the stress on various parts of a hip joint of a 160 pound individual standing at rest. The dynamic forces applied to the hip joint during a brisk walk may be as high as five times the static force applied during a stationary upright stand. FIG. 5B illustrates the stress when a force of approximately 750 pounds is applied to the joint. During a strenuous run, or jumping, the hip joint may be subject to dynamic forces as high as nine or ten times as great as the static forces experienced while standing upright. FIG. 5C indicates the stress when a force of approximately 1,400 pounds is applied to the joint.

It will be readily appreciated from FIG. 5 that the dome area of the articular surfaces, indicated generally by arrow 80, is the substantial weight bearing portion of the articular surface. Significantly, the surface area over which the increased load is distributed does not appreciably increase during walking or running.

The stress values represented in FIGS. 5A, 5B, and 5C were determined considering the attributes of a "normal" hip joint. The effect of congruency of the hip joint, as demonstrated in FIG. 4B, increases the stress applied to the articular surfaces. Thus, while under the load condition indicated in FIG. 5C, the articular dome regions of a normal hip are subjected to a pressure of nearly 2,000 psi. If the joint were congruent and responded to loading in the fashion indicated in FIG. 4B, the pressure upon the articular surface of the dome area would be significantly greater than that indicated in FIG. 5C. It is easy to appreciate why degeneration of the dome areas often occurs quite rapidly once hip congruity occurs.

Another useful tool in identifying the likely location of pain at the dome area of the hip is the placement of trabecular stress lines in the femoral neck and head. Trabecular stress lines are linear bridge-like bone structures which are apparent on gross anatomical observation of a bone or especially in radiological studies. In FIG. 6, the femoral head is indicated at 90, the greater trochanter at 92 and the lesser trochanter at 94. There are three separate "systems" of trabecular stress. The "lateral" trabecular stress system is indicated at 96 in FIG. 6, the "arcuate" trabecular stress system is indicated at 98, and the "medial" trabecular stress system, the most pertinent to the present discussion, is indicated at 100. It is thought that the medial trabecular stress system carries the load acting on femoral head 90 through the neck to the central layer of the femoral shaft. It is most likely that medial stress system 100 functions by increasing the strength of the femoral head at the dome area where the stress lines diverge.

Clinical observations and diagnostic studies further support a conclusion that the dome area is the primary region of pain in a hip joint. Observation of gross anatomical wear patterns indicates that the dome area of the acetabulum and femoral head is the region of the joint which shows the greatest involvement with degenerative disorders such as osteoarthritis. A condition known as intraosseous medullary venus hypertension (high blood pressure within the bone) is present in the dome area of the femoral head. Intraosseous hypervascularity (abnormal size and number of blood vessels within the bone) of the dome areas of both the acetabulum and the femoral head is generally present in osteoarthritis. Treatment of cysts and osteophytes in the dome regions of the femoral head and acetabulum are particularly helpful in reducing pain in the hip where degeneration of the articular cartilage surfaces has not occurred to a significant extent. Overall reduction in pain generally accompanies the treatment of these disorders in the dome region, while treatment of these disorders in other regions of the joint often produces less relief from pain.

While any one of the above-listed indications may be persuasive evidence of the role played by the dome areas in the causation of hip pain, the cumulative support provided by those indications listed above, clearly shows that degeneration of the dome area of the femoral head and/or the acetabulum is the primary location of pain in a hip afflicted with osteoarthritis and related disorders.

Having localized the major source of pain in a diseased hip, it would be beneficial to be able to either repair or replace the areas of damaged articular surfaces. The present invention is adapted to replacement of the minimum amount of these surfaces necessary to provide acceptable reduction of pain.

C. Description of the Components of the Presently Preferred Embodiments of the Present Invention Reference will now be made to FIGS. 7–11 to describe the structure of the components of the presently preferred embodiments. In the drawings, like structures are marked with like numerals.

One presently preferred embodiment of the present invention is shown in perspective in FIG. 7. As can be seen in FIG. 7, the structure of the embodiment includes two prosthetic components for use in subtotal replacement of hip joint dome surfaces. The structure includes a femoral component, generally indicated at 150, and an acetabular component, generally indicated at 110. Each of these components is discussed below.

The femoral component 150 includes a superior upward facing surface 152 which is substantially spheroidal in shape and a lower surface portion 154 which is substantially flat and is provided with fixation posts generally indicated at 156A–156C. The term spheroidal, as used herein, refers to a surface which may be either perfectly spherical, or which depart therefrom, such as being elliptical. It will be appreciated that structures other than that shown in FIGS. 7 and 8 can be used for the femoral component 150.

Femoral component 150 may be advantageously fabricated from a stainless steel alloy known in the art as 316L. Stainless steel 316L has the advantage of being easily machined, an economical method of fabrication when dealing in small quantities. Other materials of suitable strength and characteristics may of course be used.

The spheroidally shaped upper surface 152 of the femoral component 150 serves as an articular surface. When implanted on a femoral head, articular surface 152 will be disposed superiorly so as to be generally facing the direction towards the patient's head when the patient is in a standing position.

The curvature of superior articular surface 152 can be clearly seen in the cross-sectional view of FIG. 9A. The shape of superior articular surface 152 is chosen with several considerations in mind. First, the shape of superior articular surface 152 is chosen so as to closely approximate the shape of the dome area of the femoral head which femoral component 150 will be replacing. It is also important to consider the fact that articular surface 152 will be in intermittent contact with articular cartilage during sitting or arising from a seated position, and will be in prolonged contact with the patient's articular cartilage during periods of sitting. However, the contact between articular surfaces 152 and 120 with the patient's articular cartilage during sitting will be during a non-weight bearing period. Thus, this prolonged contact is not expected to result in any adverse effects on the articular cartilage This characteristic has been demonstrated by the success of using nonbiological materials on healthy cartilage in other joints of the body, for example the knee joint.

Since it is an object of the present invention to remove and replace as little bone mass as possible, the spheroidal section delineated by the shape of femoral articular surface 152 should be formed so that the angle subtended by the arc of the surface 152 i generally less than 180°. As shown in FIG. 9A, this measurement of arc is made by extending lines 162A and 162B from the points where femoral articular surface 152 intersects inferior surface 154 through the center of the radius marked $R_F$ in FIG. 9A. The angle subtended is marked G in FIG. 9A. Furthermore, as will be discussed in detail later in this disclosure, the curvature of superior articular surface 152 can be best described by measuring the radius marked F in FIG. 9A.

In the case of a nonspherical femoral articular surface, the angle marked G in FIG. 9A would be delineated by the angle formed by lines extended perpendicular to lines tangent to the surface of the articular surface.

Another way of describing angles D, E, and F shown in FIGS. 9 and 9A is to use the well-known geometrical term "sector." As can be appreciated by examining FIGS 9 and 9A, the views of the embodiment taken through the indicated planes may be said to define a sector of a generally circular geometric shape.

Accordingly, the articular surface taken through the indicated plane defines a sectoral arc. Also, a sectoral angle is formed by Angles D, E, and F. Use of the terms "sectoral arc" and "sectoral angle" with respect to the present invention is intended to be consistent with the generally accepted definitions of those terms to those familiar with such geometrical terminology.

As can be appreciated from the foregoing discussion, it is not an object to completely replace the femoral head. Rather, the present invention recognizes that in most cases it is more appropriate to replace only the diseased portion of the dome area of the joint in order to obtain satisfactory reduction of pain and enhancement of function.

The inferior, or bottom, surface 154 of femoral component 150 is generally flat and is advantageously provided with three fixation posts 156A–156C. It should be appreciated that inferior surface 154 and fixation posts 156A–156C may be of shapes other than those illustrated. When femoral component 150 is implanted, fixation posts 156A–156C are inserted into bores which are drilled into the femoral head as will be explained later. Fixation posts 156A–156C may be provided with grooves 160 to improve the fixation of femoral component 150 onto the patient's femoral head.

It should be appreciated that alternative structures could be substituted for fixation posts, such as nails or pins. The important characteristic is that inferior surface 154 of the femoral component is able to be affixed to the femoral head and provide suitable support. The femoral component illustrated in FIGS. 7–9A is designed so as to be fixed to the patient's femoral head with the use of an acrylic cement, such as PMMA.

A presently preferred embodiment of the acetabular component, generally indicated at 110, of the present invention is also illustrated in FIGS. 7–9A. The acetabular component of the embodiment illustrated in FIGS. 7–9A is preferably fabricated from ultra-high molecular weight polyethylene (UHMWP) and stainless steel 316L. UHMWP was chosen as a material for the acetabular component due to its low friction characteristic, strength, tendency to not shed particles of the material into the joint with use, and its susceptibility to both milling and molding formation techniques. Other materials, of course, may also be suitable for use in construction of the acetabular component.

The articulating surface 120 of the acetabular component will be positioned generally facing downward, or inferiorly, when positioned in the acetabulum. Thus, acetabular articular surface 120 may also be termed inferior articular surface 120.

As illustrated in FIGS. 7–9A, acetabular component 110 is advantageously provided with both UHMWP layer 112, which forms inferior articular surface 120, and backing plate 114. Backing plate 114 is used in order to provide rigidity to UHMWP layer 112 and to spread the load upon the acetabular component. It is presently preferred that UHMWP layer 112 be attached to backing plate 114 by forming retaining edges, marked 130 in FIGS. 7–9, which are capable of grasping the edges of backing plate 114 to hold UHMWP layer 112 in position. By constructing the backing plate from a material having characteristics of high rigidity and strength, the acetabular component may be made thinner than would be possible if it was constructed only from UHMWP.

The shape of acetabular articular surface 120 in the presently preferred embodiment illustrated in FIGS. 7-0 is substantially congruent with the corresponding femoral articulating surface 152. It may be advantageous under some circumstances for articular surfaces 152 and 120 to be noncongruent.

The shape of the inferior articular surface of the embodiment illustrated in FIGS. 7–9A can be best described by reference to the radii indicated in FIG. 9 and marked A, B, and C. Since the articular surfaces 120 and 152 of the embodiment shown in FIGS. 7–9A are substantially spherical, a simple radius may be used to describe the curvature of the components. Radius A, in FIG. 9, is the radius of the curvature of inferior articular surface 120 and, in the illustrated embodiment, matches radius F shown in FIG. 9A for the superior articular surface. Radius B and Radius C indicate the curvatures of the inferior and superior sides of backing plate 114. Thus, the most important dimensions of acetabular component 110 are defined by radii A, B, and C and angles D and E as shown in FIGS. 9 and 9A.

The size and shape of the surface area of acetabular component articular surface 120 is chosen with at least three considerations in mind.

First, the prosthesis should replace the damaged dome area of the acetabulum. It is necessary that enough damaged cartilage and bone be replaced so as to provide the patient relief from pain.

Second, the surface area of the acetabular component articular surface should be great enough such that most of the weight-bearing dome area of femoral articular surface 152 is in contact with the acetabular component rather than in contact with the patient's articular cartilage while the patient is standing. Acetabular articulating surface 120 should be large enough both in front-to-back dimension, (as would be taken along the sagittal plane of the body if the component were implanted), indicated by angle E in FIG. 9A, and side-to-side dimension, (as would be taken along the transverse plane of the body if the component were implanted), indicated by angle D in FIG. 9, to provide an adequate weight-bearing surface.

Third, an object of the present invention is to remove as little healthy bone as possible. Thus, it is desirable to reduce the size of both the femoral and the acetabular components as much as possible while still obtaining the desired results.

In the embodiment illustrated in FIGS. 7-9A, backing plate 114 is provided with two fixation posts 116A and 116B As with fixation posts 156A-156C, fixation posts 116A and 116B are advantageously provided with grooves 118. It is presently preferred that acetabular component 110 be fixed in place using an acrylic cement, such as PMMA. The acetabular component 110 is fixed in a recess formed in the acetabulum such that articulating surface 120 does not protrude beyond the surrounding articular cartilage when the joint is unloaded as will be described later in more detail.

An alternative presently preferred embodiment of the present invention is illustrated in FIGS. 10 and 11. The embodiment shown in FIGS. 10-11 is fabricated with the same considerations discussed above in connection with the embodiments illustrated in FIGS. 7-9A. However, the embodiment differs from the embodiments shown in FIGS. 7-9A in several respects.

Acetabular component 210 is formed from a single UHMWP layer and includes inferior articular surface 220. Also, the side-to-side dimension of acetabular component 210 is greater than the same dimension used in connection with acetabular component 110 illustrated in FIGS. 7-9A. Such changes in the structure of acetabular component 210 may be necessary in order to accommodate the particular needs of a patient. For example, UHMWP could be used without a backing plate to construct an incongruent hip prosthesis capable of becoming congruent under load, in a manner similar to a normal hip joint.

Acetabular component 210 is provided with a superior fixation surface 214 and fixation posts 216A and 216B. Fixation surface 214, as illustrated in FIG. 10, may be provided with a porous bony ingrowth surface as indicated generally at 218. Porous bony ingrowth surface 218 allows the growth of bone within the structures provided on surface 218 such that the acetabular component 210 becomes rigidly fixed to the underlying bone structure as the bone grows into the porous bone ingrowth surface 216.

Femoral component 250, illustrated in FIGS. 10 and 11, includes superior articular surface 252 which is formed utilizing the same considerations mentioned in connection with acetabular component 150 illustrated in FIGS. 7-9A. However, inferior fixation surface 154 in FIG. 11 is advantageously provided with a single fixation post 256 rather than the three fixation posts 156A-156C used in connection with the embodiment pictured in FIGS. 7-9A. Since stresses applied to the femoral and acetabular components of the present invention will be directly on the articular surfaces, with little or no sideways pressure, it is anticipated that dislodgement of the prosthetic components will not be a significant problem. It is anticipated that it would be possible in some circumstances to merely press-fit the femoral or acetabular components without the need to cement them in place.

By fabricating femoral and acetabular components in accordance with the foregoing description, it has been found possible to significantly reduce hip pain due to disorders affecting cartilage in the dome area of the hip. Having described the structures used in the present invention, the associated method and the protocols used to determine when the procedure would be appropriate will next be discussed.

D. Description of the Procedures and Protocols of the Presently Preferred Embodiments of the Present Invention The present invention will have application in reducing pain due to several hip disorders, and is particularly indicated for use in cases involving osteoarthritis of the hip.

A candidate for implantation of the present invention is preferably chosen by considering several factors. Generally, a patient seeking out the advice of an orthopedic surgeon complains of hip pain and stiffness of the joint with accompanying diminished function. An examination of such a patient may reveal a limp, and perhaps some discrepancy in the individual's limb length. A radiological examination will often verify a diagnosis of osteoarthritis of the hip. Depending upon the classification of the condition and the particular suitability of the patient for the procedure, the patient will either be accepted or rejected as a candidate for the present invention.

In the present invention, since a large portion of the patient's articular surfaces are saved, the size and shape of the prosthetic components of the present invention must be selected so as to properly complement the shape of the patient's articular surfaces which remain. Thus, it is necessary by the use of radiological and other examination techniques to carefully determine which size and shape of both the femoral and acetabular components would be best suited for a particular patient. It is anticipated that availability of a series of various sized and shaped prostheses will allow the surgeon to select a set which will provide an appropriate fit for a particular patient.

The presently preferred method of the present invention provides that the patient would be prepared preoperatively in a fashion very similar to that generally used for major hip surgery, such as a total hip replacement. Due to the less invasive nature of the subtotal arthroplasty procedure, the risk of infection is significantly less than following a total arthroplasty.

Once the patient is taken to the operating room, the patient is placed in a supine position and the draping and preparation of the hip is completed, and the patient is anesthetized. While many surgical approaches to the hip may be used in the present invention, the presently preferred method is a straight lateral approach. Such an approach bisects the greater trochanteric area. The incision is preferably approximately six inches proximal to the greater trochanter continuing to about three inches distal from it. The incision is deepened through subcutaneous tissues while hemostasis is obtained by electrocutery. The gluteal muscles are then retracted to expose the hip joint capsule.

The trochanteric bursa is excised and the vastus lateralis is transected. A trochanteric osteoectomy is then performed. The greater trochanter is removed to allow the surgeon better access to, and view of, the structures of the hip during the procedure. The abductor muscles are then dissected off from the capsule of the hip and retracted and held proximally with a retractor and two Steinmann nails driven into the ilium. A partial capsulectomy is performed and the tip dislocated posteriorly such that the acetabulum is easily viewable.

The surgeon examines the acetabulum and the femoral head to determine the best location for the components of the present invention. The acetabulum is then prepared by using one or more templates used to guide the surgeon during cutting by appropriately shaped power driven burrs. The templates are fashioned so as to match the size and shape of the acetabular component of the present invention. By using templates the exact position of the acetabular component may be visualized by the surgeon and the templates act as a precise guide for preparing the acetabulum for receiving the present invention.

For example, one template that may be used outlines the perimeter shape of the acetabular component. This template is placed on the acetabular surface and used as a guide by the surgeon for removing the bone of the acetabulum to a proper depth and to a proper shape. Another template might also be used to indicate to the surgeon the exact location of the bores that must be formed in order to accommodate the fixation posts provided on the fixation surface of the acetabular component.

As shown in FIG. 12, a recess, generally indicated at 304, is formed in the acetabulum so as to accommodate the acetabular component 306 in an inlaid fashion. Such a recess requires that portions of the acetabular surface be removed, preferably by using a high speed power driven burr. The edges 314 of recess 304 are preferably finished so as to be vertical and to match the edges of the acetabular component 306. Likewise, floor 316 of recess 304 should be shaped so as to precisely match the shape of the fixation surface of the acetabular component 306.

After recess 304 and anchoring holes 318 have been formed, as shown in FIG. 12, the acetabular surface is thoroughly cleansed with a pulsating water lavage and antibiotic irrigation. The acetabular component is next inserted and secured in place by the use of PMMA. As noted above, other methods, such as those using porous bone ingrowth techniques, may be used to fix the acetabular component in place.

Once the acetabular component is inserted, the excess PMMA is removed from the articular surface such that no PMMA extends past the acetabulum articular surface. The acetabular component is inserted to a depth such that the articular surface of the acetabular component and the surface of the articular cartilage of the acetabulum are at precisely the same level.

The surgeon next uses a reciprocating saw to remove a portion of the femoral head as illustrated in FIG. 12. The cut should be of substantially the same shape as the fixation surface of the femoral component.

Any bone cysts which are found present on the femoral head should be curretted out and all dead bone also removed. Anchoring holes 320 are formed to receive the femoral component. As with the acetabular component, a template may be used to guide the surgeon. Anchoring bores 320 are drilled to "bleeding bone" to determine the vitality of the underlying bone stock. Once the femoral head has been cut to provide a surface suitable for receiving the femoral component fixation surface and anchoring bores have been formed, the femoral head is cleansed and washed in an antibiotic solution.

Low viscosity PMMA is pressurized into the cancellous surface of the bone and the appropriate femoral component is fit into place and held in position until the PMMA sets. Low viscosity PMMA is preferred to fix the femoral component of the present invention in order to provide better penetration of the PMMA into the cancellous bone structure and thus provide better fixation. The excess PMMA is removed and the prosthesis is examined for proper placement.

Once both the prosthetic components are in place to the satisfaction of the surgeon, as shown in FIG. 13, the hip is reduced and articulated. FIG. 14 is a partial cross section showing the implanted prosthetic components in the reduced hip joint. Antibiotic irrigation is once again carried out to reduce the possibility of infection.

The greater trochanter, with its attached abductors, is then reattached to its bed at the trochanteric base by the use of screws or nails. The greater trochanter is preferably reinforced by suturing the cut edge of the vastus lateralis to the trochanteric cut edge with a heavy nonabsorbable suture. The hip is then fitted with two drains brought out anteriorly from the depths of the wound. The remaining muscle and tissue of the surgical wound is then closed and dressed. Once the surgical procedure is completed, the patient is taken to recover post-operatively, and X-rays are once again obtained to check the results of the procedure.

In order to more fully appreciate the application of the present invention, a few examples are presented below. These examples are to be considered in all respects as illustrative, and not limiting.

EXAMPLE 1

This example involved a seventy-four (74) year old white male who had previously undergone a left total hip arthroplasty and bilateral total knee arthroplasties. Just previously to implantation of the structures of the present invention, the patient had significant pain in his hip upon standing, sitting, and even at rest. Particularly noticeable was a limp as well as the fact that the patient was unable to flex his legs very well. His walking capacity had diminished to approximately one block before a rest was necessary. Having undergone several arthroplasties the patient was well acquainted with the risks and potential benefits of another arthroplasty and was deemed to be a suitable candidate for subtotal hip arthroplasty.

The prosthetic components of the present invention implanted in this patient were substantially similar to those illustrated in FIGS. 7-9A.

The dimensions of the components implanted in the patient of Example No. 1 which correspond to the radii and angles shown in FIGS. 9 and 9A are:

| Radius | Measurement (millimeters) |
|---|---|
| A | 23.75 |
| B | 27.75 |
| C | 29.25 |
| F | 23.75 |

| Angles | Measurement (degrees) |
|---|---|
| D | 90 |
| E | 120 |
| G | 78 |

By ten months following the subtotal dome arthroplasty of this patient, he had experienced a 91% reduction in pain while standing and walking, and experienced no pain while sitting or while seated. He experiences some slight pain when arising from a seated position, similar to that experienced in his other total hip replacement.

This patient experienced a normal range of motion in his hip repaired by subtotal dome arthroplasty, in contrast with only an 85% range of motion in the hip repaired by a conventional total hip.

The patient has not experienced any complications from implantation of the subtotal dome prosthesis, and X-ray studies indicate the prosthesis remains firmly in place.

EXAMPLE 2

A fifty-five (55) year old white male with no other joints involved with any degenerative disorder had a limited range of motion in all spheres. His walking capacity was significantly diminished. An X-ray examination confirmed the diagnosis of superior lateral osteoarthritis of the right hip. After consultation with the patient, he was deemed a suitable candidate for implantation of the present invention.

The prosthetic components of the present invention implanted in this patient were substantially identical to those illustrated in FIG. 7-9A.

The dimensions of the components implanted in the patient of Example No. 2 which correspond to the radii and angles shown in FIGS. 9 and 9A are:

| Radius | Measurement (millimeters) |
|---|---|
| A | 23.75 |
| B | 27.75 |
| C | 29.25 |
| F | 23.75 |

| Angles | Measurement (degrees) |
|---|---|
| D | 90 |
| E | 120 |
| G | 91 |

Nine and one-half months following subtotal dome arthroplasty, this individual reported a 93% reduction in pain during walking, and reported that he experienced no pain when standing or sitting. He experiences some discomfort on arising when he has been seated for a long while.

This individual has no limp, and lifts relatively heavy objects at his place of employment without difficulty. He has experienced no complications, and X-rays do not demonstrate any changes that would cause any concern about the integrity of the subtotal prosthesis.

EXAMPLE 3

Figure 1:
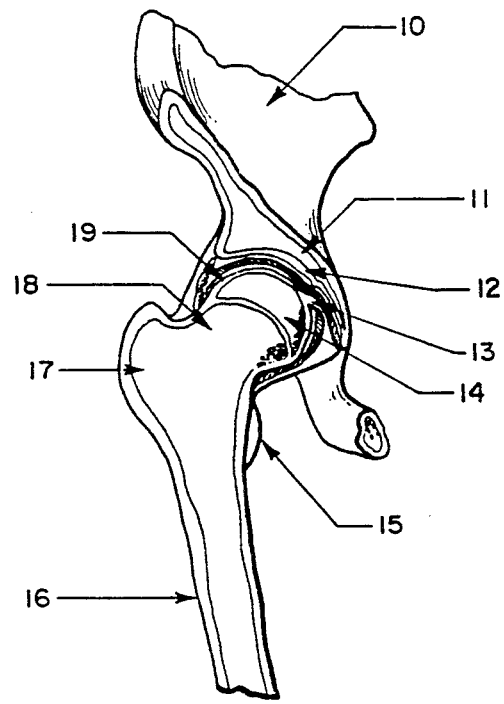
FIG. 1 is a cross-sectional view showing the major structures of the human hip joint.
Figure 2:
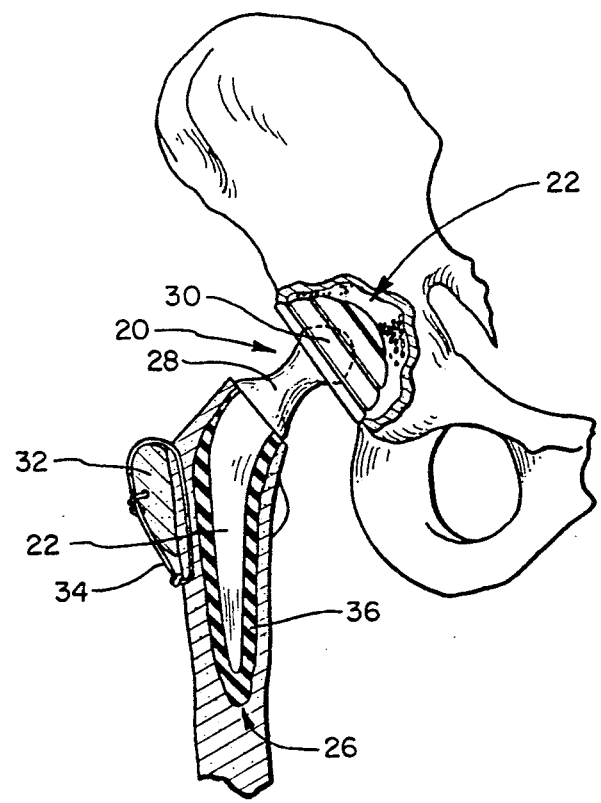
FIG. 2 is a partial cross-sectional view of a human hip in which a total hip replacement common in the prior art has been implanted to replace the natural hip joint.

The patient of Example 3 was a fifty-five (55) year old white male who had undergone two previous hip arthroplasties on his left hip. One arthroplasty was an interpositional type which was later revised to a standard total hip prosthesis similar to that illustrated in FIG. 2. This patient exhibited the classical symptoms of osteoarthritis of the right hip in that he experienced pain while standing, walking, climbing stairs, and also stiffness as he attempted to stand or sit.

The prosthetic components implanted were again substantially similar to those illustrated in FIGS. 7-9. Their dimensions corresponding to the radii and angles shown in FIGS. 9 and 9A are:

| Radius | Measurement (millimeters) |
|---|---|
| A | 26.0 |
| B | 30.0 |
| C | 31.5 |
| F | 26.0 |

| Angles | Measurement (degrees) |
|---|---|
| D | 90 |
| E | 120 |
| G | 101 |

By nine months following subtotal hip arthroplasty in this patient, he was reporting a 78% reduction in pain during walking and no pain while standing or sitting. He reported an occasional "catching" when arising. This patient has an improving limp occasioned by muscle weakness; both the limp and experienced pain are improving as the patient's muscle strength continues to improve.

This patient experienced a fall down a flight of ten stairs without any untoward effects to his subtotal prosthesis, and reports that he is very satisfied with the subtotal hip arthroplasty.

V. SUMMARY

From the foregoing discussion and description it will be appreciated that the present invention provides structures and methods for reducing pain in a hip joint when the dome area of the joint has become involved in a degenerative disorder. The acetabular and femoral components of the present invention may be fabricated to any suitable shape or size so as to fit the needs of the particular patient. Most importantly, the present invention may be utilized with relatively little invasion of the structures of the human body as compared to those structures and methods utilized in the prior art.

Still further, the present invention provides that relatively little foreign material is implanted in the body. Also, the present invention is adaptable so as to allow the components of the present invention to be fixed in their proper positions using a variety of structures and methods.

By reducing the amount of foreign material implanted into a patient's body, the potential reactions due to hypersensitivity, long-term toxicity, or carcinogenicity are reduced. Since the present invention requires less invasion of the body and body structures than other structures and methods available in the prior art, the likelihood of either mild and devastating infections is also greatly reduced. Furthermore, since the femoral cavity, a region with a high-volume blood flow, is not invaded, the patient loses only a minimal amount of blood during the procedure. This also reduces the risks which attend the use of some acrylic adhesives, such as PMMA, since absorption into the blood is less likely.

Because of the integral structure of the components of the present invention, particularly of the compactness of the femoral component of the present invention in comparison with the femoral components of common total hip replacement systems, the components of the present invention are much less likely to fail due to loosening or fracture. Also, since the present invention requires removal of very little bone mass, revision of the procedure is much simpler than revision of prior art procedures. Because of the configuration of the present invention, not only should it last longer, but if revision does become necessary, it presents significantly fewer difficulties than revision of the total hip replacement found in the prior art. In fact, the total hip replacement procedure as presently practiced would be an available alternative if the present invention was found to be ineffective in a particular patient.

Thus, the present invention applies structures and methods for subtotal hip dome arthroplasty which reduce hip pain and improve hip function and avoid many of the problems experienced with prior art structures and methods while being capable of being carried out and embodied in a variety of fashions. The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A subtotal prosthesis for repairing a patient's hip joint, comprising:
    a femoral component adapted for affixation to the patient's femoral head after removal of a first portion of the patient's femoral head, said first portion including at least some of the dome area of the femoral head and substantially less than all of the patient's femoral head articular surface, the femoral component comprising:
        a superior articular surface having a shape which is less than a convex hemispheroid, the curvature of the superior articular surface substantially approximating the curvature of the removed first portion area of the patient's femoral head, the perimeter of the articular surface being substantially configured such that, when the femoral component is affixed to the remaining portion of the femoral head, the perimeter of the articular surface and the femoral head articular surface mate to form a substantially continuous articular surface; and
        an inferior fixation surface including means for securely affixing the femoral component to the remaining bone mass of the femoral head;
    an acetabular component adapted for affixation into a recess formed in the patient's acetabulum at a location opposite the femoral component which has been affixed to the femoral head when the hip joint is in a weight-bearing posture position, the acetabular component comprising:
        an inferior articular surface comprised of a material forming a low friction interface with the superior articular surface of the femoral component, the inferior articular surface having a concave curvature substantially congruent with the curvature of the superior articular surface of the femoral component, the inferior articular surface having a perimeter shape longer in a first direction than in a second direction such than when the acetabular component is fixedly secured within the recess in the patient's acetabulum the first direction is oriented in a substantially anterior-posterior direction; and
        means for securely affixing the acetabular component within the recess formed in the patient's acetabulum such that the inferior articular surface and the patient's acetabulum articular surface form a substantially continuous articular surface such that the implantation of the femoral and acetabular components effect a subtotal hip joint arthroplasty.

2. A prosthesis as defined in claim 1, wherein a sectoral angle is formed by the intersecting radii of the superior articular surface and said sectoral angle is less than approximately 180 degrees.

3. A prosthesis as defined in claim 1, wherein the perimeter of the superior articular surface is circular.

4. A prosthesis as defined in claim 1, wherein a sectoral angle is formed by the intersecting radii of the inferior articular surface in the sagittal plane of the patient's body and the first sectoral angle is less than about 180 degrees.

5. A prosthesis as defined in claim 4, wherein a second sectoral angle is formed by the intersecting radii of the inferior articular surface in the transverse plane of the patient's body and the second sectoral angle is less than about 120 degrees.

6. A prosthesis as defined in claim 5, wherein the superior fixation surface comprises a metal and the inferior articular surface comprises ultra high molecular weight polyethylene.

7. A prosthesis as defined in claim 6, wherein the acetabular component further comprises a backing plate, the backing plate being fabricated from a metal and the inferior articular surface being bonded to a first side of the backing plate and the superior fixation surface being formed on a second side of the backing plate.

8. A subtotal prosthesis for reducing pain and enhancing function of a patient's hip joint which has been damaged by trauma or degenerative disease, comprising:
    a femoral prosthetic component adapted to replace at least a portion of the weight-bearing dome area of a patient's femoral head which has been damaged, and substantially less than all of the patient's femoral head articular surface, said femoral component including:
        a superior articular surface having a convex shape and forming less than a hemispheroid, the articular surface having a curvature approximating the curvature of the removed portion of the patient's femoral head; and
        femoral fixation means positioned on the inferior side of the femoral prosthetic component for fixing the femoral prosthetic component to the patient's femoral head which remains after the removal of substantially less than all of the femoral head including the portion of the weight-bearing dome area of the patient's femoral head such that the femoral head articular surface and the femoral component superior articular surface form a substantially continuous articular surface and the remainder of the patient's femoral head articular surface and femur is left intact; and an acetabulum component, said acetabulum component adapted to replace substantially less than all of the patient's acetabulum including at least a portion of the weight-bearing dome area of the patient's acetabulum opposing the position of the femoral component when affixed upon the femoral head when the hip joint is in a weight-bearing posture position, the acetabulum component including:

an inferior articular surface having a concave shape and forming less than a hemispheroid, the curvature of the inferior articular surface substantially complementing the curvature of the superior articular surface so as to be congruent therewith; and backing plate means positioned on the superior side of the acetabulum component, the backing plate means including means for fixing the acetabulum component into a recess formed in the patient's acetabulum such that the inferior articular surface and the articular surface of the patient's acetabulum form a substantially continuous articular surface; and the inferior and the superior articular surfaces comprising materials forming a low friction interface such that the prosthesis is capable of supporting the weight of the patient and effecting a subtotal hip arthroplasty.

9. A prosthesis as defined in claim 8, wherein the superior articular surface forms a first arc and the radii taken from the end points of the first arc form an angle which is less than approximately 180 degrees.

10. A prosthesis as defined in claim 8, wherein a second arc is formed by the inferior articular surface in the sagittal plane of the patient's body and the radii taken from the end points of the second arc form an angle which is less than about 180 degrees.

11. A prosthesis as defined in claim 10, wherein a third arc is formed by the inferior articular surface in the transverse plane of the patient's body and the radii taken from the end points of the third arc form an angle which is less than about 120 degrees.

12. A prosthesis as defined in claim 8, wherein the superior articular surface is fabricated from a metal and the inferior articular surface is fabricated from ultra high molecular weight polyethylene.

13. A prosthesis as defined in claim 8, wherein the acetabulum component further comprises a backing plate the backing plate being fabricated from a metal and the inferior articular surface being bonded to a first side of the backing plate and the superior fixation surface being formed on a second side of the backing plate.

14. A subtotal prosthesis for repairing a patient's damaged hip joint comprising:

a femoral component adapted to replace only a first portion of the patient's femoral head, said first portion of the patient's femoral head corresponding approximately to the dome area of the femoral head, said femoral component including:

a superior articular surface being generally shaped as less than a convex hemispheroid, the superior articular surface having a curvature approximating the curvature of the first portion of the patient's femoral head and generally replacing the damaged articular surface of the patient's femoral head; and an inferior fixation surface, said inferior fixation surface including means for fixing the femoral component on the femoral head in place of the removed first portion while leaving the remaining bone of the femur substantially intact; and an acetabulum component being adapted to replace only a first portion of the patient's acetabulum, said first portion of the acetabulum corresponding to the first portion of the patient's femoral head, said acetabulum component including:

an inferior articular surface being generally shaped so as to congruently correspond to the curvature of the superior articular surface, the inferior articular surface having a first dimension which is less than a second dimension, the inferior articular surface and the superior articular surface comprising materials which when in contact in the hip joint form a low friction interface; and means for fixing the acetabulum component within a recess formed in the patient's acetabulum such that the inferior articular surface and the patient's acetabulum articular cartilage form an approximately continuous articular surface and such that the superior and inferior articular surfaces bear a substantial amount of the patient's weight when the hip is in a weight-bearing posture such that the femoral and acetabulum components effect a subtotal hip dome arthroplastry.

15. A method of repairing a patient's damaged hip joint, comprising the steps of:

providing a femoral arthroplasty component comprising a superior articulating surface, said superior articulating surface shaped as a convex hemispheroidal section;

removing at least a portion of the weight-bearing dome area of the femoral head and substantially less than all of the patient's femoral head;

fixing the femoral arthroplasty component on the remaining portion of the femoral head such that the superior articulating surface and the articular surface of the femoral head form a substantially continuous articular surface;

providing an acetabulum arthroplasty component comprising an inferior articulating surface, said inferior articulating surface having a curvature approximately congruent tot he curvature of the inferior articulating surface;

removing substantially less than all of the patient's acetabulum to form a recess in the acetabulum articular surface, the acetabulum surface which is removed being that which substantially interfaces with the portion of the femoral head which was removed when the hip joint is in a weight-bearing posture position; and fixing the acetabulum component in the recess formed in the patient's acetabulum in order that the inferior articulating surface and the acetabulum articular surface form a substantially continuous articular surface and such that when the hip joint is in a weight-bearing posture the femoral arthroplasty component and the acetabulum arthroplasty component bear a substantial portion of the patient's weight so as to effect a subtotal hip arthroplasty.

16. A method as defined in claim 15 wherein the fixation means comprises at least one fixation post and wherein the step of fixing the femoral arthroplasty component comprises the steps of:
   forming at least one bore in the femoral head;
   inserting at least one fixation post into at least one bore; and
   securing the femoral component on the femoral head.

17. A method as defined in claim 15, wherein the step of providing a femoral arthroplasty component comprises the step of forming the superior articular surface so as to approximate the dome area of the patient's femoral head and limiting the angle subtended by the arc formed by the superior articular surface such that unnecessary removal of bone and cartilage is avoided.

18. A method as defined in claim 15, wherein the step of fixing the femoral component on the femoral head comprises the step of making a transverse cut across a chord of the hemispheriod formed by the articular surface of the femoral head.

19. A method as defined in claim 15, wherein the step of fixing the femoral component on the femoral head comprises the step of securing the femoral component on the femoral head such that the articular surface of the femoral head and the superior articular surface form a substantially continuous articular surface.

20. A method as defined in claim 15, wherein the steps of providing a femoral component and providing an acetabular component comprise forming the superior articular surface and the inferior articular surface of materials that, when implanted in the patient's hip joint, form a low-friction interface capable of bearing the weight of the patient.

21. A method as defined in claim 15, wherein said steps of removing a portion of the femoral head comprise removing an amount of bone from the patient's femoral head so as to not cause invasion of the femoral canal.

22. A method as defined in claim 15, wherein the step of providing an acetabular component comprises the step of forming an acetabular component comprising an articular surface having perimeter dimensions such that the inferior articular surface, when fixed in the patient's acetabulum, provides a low friction interface with at least a portion of the superior articular surface during the weight bearing intervals of hip joint movement during a normal walk.

23. A method as defined in claim 15, wherein the step of providing an acetabular component comprises the steps of:
   forming an inferior articular surface of a material providing a low friction interface with the femoral component;
   forming a backing plate capable of supporting the articular surface; and
   securing the inferior articular to the backing plate.

24. A method as defined in claim 15, wherein the step of fixing the acetabular component in the patient's acetabulum comprises the steps of:
   forming a recess in the patient's acetabulum; and
   securing the acetabular component in the recess such that the acetabulum articular surface and the inferior articular surface form a substantially continuous surface.

25. A method as defined in claim 15 wherein the patient's hip joint has been damaged by a degenerative disease.

26. A method as defined in claim 15 wherein the patient's hip joint has been damaged by trauma.

27. A method of reducing pain and enhancing function of a patient's hip joint in which the articular cartilage has been damaged or diseased, the method comprising the steps of:
   removing at least a portion of the weight-bearing dome area of the patient's femoral head and substantially less than all of the patient's femoral head;
   providing a femoral arthroplasty component comprising a superior articulating surface, the superior articulating surface being generally shaped as less than a convex hemispheroid so as to approximate the shape of the femoral head articular surface;
   fixing the femoral arthroplasty component in the location where the portion of the femoral head was removed such that the superior articular surface simulates the articular surface of the patient's femoral head;
   forming a recess in the patient's acetabulum in a location opposite from the position of the femoral component when the hip is in a weight-bearing posture position;
   providing an acetabulum arthroplasty component comprising an inferior articular surface, said inferior articular surface having a curvature congruent with the curvature of the superior articular surface and said inferior articular surface comprising a material which provides for a low friction interface to be formed when the superior and inferior articular surfaces are in contact with each other in the human body; and
   fixing the acetabulum component in the recess formed in the patient's acetabulum such that the inferior articular surface forms a substantially continuous articular surface with the articular surface of the patient's acetabulum and such that the interface between the femoral and acetabulum components bears a substantial portion of the force on the hip joint when the hip joint is in a weight-bearing posture, such that the implanted femoral and acetabulum components effect a subtotal hip dome arthroplasty.

28. A subtotal prosthesis for repairing a patient's hip joint which has been damaged due to trauma or disease, comprising:
   a femoral prosthetic component adapted to replace at least a portion of the weight-bearing dome area of the patient's femoral head which has been damaged, and substantially less than all of the patient's femoral head, said femoral component including:
      a superior articular surface having a convex shape and forming less than a hemispheroid, the articular surface having a curvature approximating the curvature of the removed portion of the patient's femoral head; and
      femoral fixation means positioned on the inferior side of the femoral prosthetic component for fixing the femoral prosthetic component to the patient's femoral head which remains after the removal of substantially less than all of the femoral head such that the remainder of the patient's femoral head articular surface and femur is left intact; and an acetabulum component, said acetabulum component adapted to replace substantially less than all of the patient's acetabulum including at lest a portion of the weight-bearing dome area of the patient's acetabulum opposing the position of the femoral component when affixed upon the femoral head when the hip joint is in a weight-bearing posture position, the acetabulum component including:

an inferior articular surface having a concave shape and forming less than a hemispheroid, the curvature of the inferior articular surface substantially complementing the curvature of the superior articular surface so as to be substantially congruent therewith, the perimeter of the inferior articular surface being of a generally circular shape; and backing plate means positioned on the superior side of the acetabulum prosthetic component, the backing plate means including means for fixing the patient's acetabulum such that the inferior articular surface and the patient's acetabulum form a substantially continuous articular surface;

the inferior and the superior articular surfaces comprising materials forming a low friction interface such that the prosthesis is capable of supporting the weight of the patient and effecting a subtotal hip arthroplasty.

* * * * *

UNITED STATES PATENT AND TRADEMARK OFFICE
CERTIFICATE OF CORRECTION

PATENT NO. : 5,127,920
DATED : July 7, 1992
INVENTOR(S) : A. CREIG MACARTHUR It is certified that error appears in the above-identified patent and that said Letters Patent is hereby corrected as shown below:

```
Title page, column 1, line 1, "PROSTHESIS" should be --PROSTHESES--
Column 1, line 2, "PROSTHESIS" should be --PROSTHESES--
Column 1, line 44, "actabulum 11" should be --acetabulum 11--
Column 1, line 46, "illium 10" should be --ilium 10--
Column 1, line 49, "speroidally" should be --spheroidally--
Column 3, line 66, "prosthesis" should be --prostheses--
Column 5, line 26, after "stream" insert --.--
Column 8, line 52, "providing" should be --to provide--
Column 9, line 53, "illium" should be --ilium--
Column 10, line 59, after "joint" insert --,--

Column 15, line 35, after "116B" insert --.--
Column 28, line 6, after first occurrence of "the" insert --acetabulum
component into a recess formed in the--
```

Signed and Sealed this

Twenty-eighth Day of December, 1993

*Attest:*

BRUCE LEHMAN

*Attesting Officer*  *Commissioner of Patents and Trademarks*